(12) United States Patent
Schneider et al.

(10) Patent No.: US 8,827,950 B2
(45) Date of Patent: Sep. 9, 2014

(54) CATHETER

(75) Inventors: Ralph Schneider, Rangendingen (DE); Judith Hartwig, Dotternhausen (DE); Stevan Nielsen, Rottenburg (DE)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 138 days.

(21) Appl. No.: 13/324,922

(22) Filed: Dec. 13, 2011

(65) Prior Publication Data

US 2012/0150108 A1 Jun. 14, 2012

Related U.S. Application Data

(62) Division of application No. 10/725,374, filed on Dec. 3, 2003, now Pat. No. 8,105,311.

(30) Foreign Application Priority Data

Dec. 11, 2002 (EP) ..................... 02027767

(51) Int. Cl.
*A61M 29/00* (2006.01)
(52) U.S. Cl.
USPC ..................................... 604/96.01
(58) Field of Classification Search
USPC .......... 604/96.01, 103.09, 270, 523, 524, 533
See application file for complete search history.

(56) References Cited

U.S. PATENT DOCUMENTS

| 4,465,482 A | 8/1984 | Tittel |
| 4,569,347 A | 2/1986 | Frisbie |
| 5,405,316 A | 4/1995 | Magram |
| 5,443,448 A | 8/1995 | DeVries |
| 5,569,200 A | 10/1996 | Umeno et al. |
| 5,573,520 A | 11/1996 | Schwartz et al. |
| 5,599,326 A | 2/1997 | Carter |
| 5,741,429 A | 4/1998 | Donadio, III et al. |
| 5,800,451 A | 9/1998 | Buess et al. |
| 5,902,254 A | 5/1999 | Magram |
| 6,004,291 A | 12/1999 | Ressemann et al. |
| 6,048,338 A | 4/2000 | Larson et al. |
| 6,336,914 B1 | 1/2002 | Gillespie |
| 6,387,075 B1 | 5/2002 | Stivland et al. |
| 6,387,076 B1 | 5/2002 | Landuyt |
| 6,475,209 B1 | 11/2002 | Larson et al. |
| 8,105,311 B2 | 1/2012 | Schneider et al. |
| 2002/0177800 A1 | 11/2002 | Bagaoisan et al. |
| 2004/0068312 A1 | 4/2004 | Sigg et al. |
| 2004/0127934 A1 | 7/2004 | Gilson et al. |

FOREIGN PATENT DOCUMENTS

| CA | 2085978 | 10/1992 |
| DE | 3907549 | 9/1990 |
| EP | 0792655 | 9/1997 |
| EP | 0937480 | 8/1999 |
| FR | 1290933 | 4/1962 |
| WO | WO 9218193 | 10/1992 |
| WO | WO 9616690 | 6/1996 |

OTHER PUBLICATIONS

U.S. Appl. No. 10/725,374, Jun. 17, 2005, Office Action.
U.S. Appl. No. 10/725,374, Mar. 9, 2006, Office Action.

(Continued)

*Primary Examiner* — Aarti B Berdichevsky
(74) *Attorney, Agent, or Firm* — Workman Nydegger; Jonathan Feuchtwang

(57) ABSTRACT

A catheter is configured to prevent kinking of a catheter during handling or mounting of a pressure device. The catheter has a proximal end of its catheter shaft that is provided with a bending section having a flexibility greater than that of the section of the catheter shaft joining the proximal end.

16 Claims, 3 Drawing Sheets

(56) References Cited

OTHER PUBLICATIONS

U.S. Appl. No. 10/725,374, Sep. 7, 2006, Office Action.
U.S. Appl. No. 10/725,374, Nov. 16, 2006, Office Action.
U.S. Appl. No. 10/725,374, Apr. 16, 2008, Office Action.
U.S. Appl. No. 10/725,374, Oct. 1, 2008, Office Action.
U.S. Appl. No. 10/725,374, Jun. 26, 2009, Office Action.
U.S. Appl. No. 10/725,374, Jan. 19, 2010, Office Action.
U.S. Appl. No. 10/725,374, Aug. 3, 2010, Office Action.
U.S. Appl. No. 10/725,374, Dec. 21, 2010, Office Action.
U.S. Appl. No. 10/725,374, Sep. 28, 2011, Notice of Allowance.

CATHETER

CROSS-REFERENCE TO RELATED APPLICATIONS

This application is a division of U.S. application Ser. No. 10/725,374, filed Dec. 3, 2003, now U.S. Pat. No. 8,105,311, which claims priority to European Patent Application No. 02027767.9, filed Dec. 11, 2002, the contents of each of the foregoing applications are incorporated herein, in their entirety, by this reference.

BACKGROUND OF THE INVENTION

1. Field of the Invention

This invention generally relates to a catheter that is not prone to kinking.

2. Background Information

A generic catheter is disclosed in U.S. Pat. No. 5,569,200, which basically comprises a catheter shaft that is normally designated as a "hypotube". A fitting, preferably in the form of a luer fitting, is provided at the proximal end of said catheter shaft and serves to connect a pressure device via which pressurized fluid is introduced through channels provided in the fitting so as to expand the balloon at the distal end of the catheter shaft.

In view of the above, there exists a need for an improved catheter. This invention addresses this need art as well as other needs, which will become apparent to those skilled in the art from this disclosure.

SUMMARY OF THE INVENTION

Investigations conducted within the scope of the present invention have shown that the transition point between hypotube and fitting is very sensitive to kinking. The user may kink the catheter shaft when removing the shaft from the packaging and the protective cover or when connecting the pressure device. Investigations conducted within the scope of the present invention have shown that at least one of the reasons for said undesired kinking is the fact that the catheter shaft has a very small diameter so that, when removing the catheter shaft from the packaging or when connecting the pressure device, the user does not feel the catheter shaft in a sufficiently distinct way and may thus kink it without intention Kinking is particularly critical for the reason that it may lead to an occlusion of the inflation lumen, which makes the catheter inoperative.

It is therefore the object of the present invention to provide a catheter which has improved handling characteristics and is particularly not prone to kinking This object is achieved through a catheter comprising a catheter shaft including a proximal end and a distal end having preferably secured thereto a balloon, and a fitting, preferably a luer fitting, arranged at the proximal end of the catheter shaft. The proximal end of the catheter shaft can include a bending section.

Although the generic prior art according to U.S. Pat. No. 5,569,200 refers to the sensitivity to kinking and to the provision of slits in the catheter shaft as a possible solution for this problem, slits are provided at the distal end, at which point no forces are acting in a direction transverse to the longitudinal axis of the catheter, since there are only forces applied in the direction of the longitudinal axis of the catheter. In this respect the slits cannot solve the above-explained problem because in the generic catheter there is still the risk of kinking or even breaking upon application of external forces, as has been described above.

By contrast, the deliberate provision of a bending section at the proximal end of the catheter shaft in accordance with the invention solves the technical problem underlying the invention in a surprisingly simple and unforeseeable way because the deliberate provision of a bending section exactly in the critical region of the catheter shaft that is particularly sensitive to kinking in the generic catheter creates increased flexibility which, although it permits an intended bending, reliably prevents undesired kinking or even breaking because a plastic deformation of the catheter shaft is prevented.

U.S. Pat. No. 6,387,075 discloses a further catheter which has a spiral cut into the hypotube distally of the woven catheter shaft. Said spiral, however, is just meant to improve the flexibility of the catheter shaft in the distally situated region of the catheter. Therefore, according to the above-mentioned U.S. Pat. No. 5,569,200, the spiral cannot prevent the risk of kinking of the catheter behind the fitting.

Furthermore, it is described in U.S. Pat. No. 6,387,075 that for preventing kinking of the catheter behind the fitting the proximal catheter shaft is reinforced with a polymer over a length of about 6 to 12 inches or stabilized by way of reinforcement. Said reinforcement, however, just shifts the point of kinking in distal direction towards the end of the reinforcement. Moreover, the polymer reinforcement reduces the available and usable length of the catheter, thus resulting in an undesired extension of the catheter shaft.

Finally, in a further embodiment for reinforcing the proximal catheter shaft, U.S. Pat. No. 6,387,075 describes a catheter whose proximal shaft consists, instead of a hypotube, of a woven fabric placed between an inner and an outer polymer tube. This embodiment avoids the problem of kinking of the catheter by installation of a catheter section that does not consist of the hypotube, but is made up of novel additional shaft components. This, however, entails considerable drawbacks due to reduced pushability and a troublesome and expensive production of the catheter.

When the bending section of the present invention is designed as a cut-in spiral or as a plurality of offset cuts or incisions with suitable seals, this will entail the advantage that the bending section can be produced in a very simple manner without the use of additional materials, which reliably prevents damage to the catheter shaft. This yields a deliberate weakening of the material that leads to the desired increase in flexibility and thus kink protection.

According to another aspect of the present invention, the bending section is designed as a soft-annealed material section of the catheter shaft which in a particularly advantageous embodiment can be surrounded by a spiral spring for enhancing the stability thereof.

As a rule, it is also possible to form the bending section as a transitional section of the fitting from a flexible plastic material, which in a particularly preferred embodiment has an undercut which can be engaged by a complementary holding member of the proximal end of the catheter shaft for securing the position.

In a further alternative embodiment, the bending section is formed by a plurality of balls which are mounted on the proximal end of the catheter shaft. The balls can be provided on the catheter shaft (hypotube) either mechanically, or they may be formed thereon by an adhesive, by welding or as one piece. Furthermore, it is possible to provide a heat shrinkable tube over the balls for fixing the position.

One object according to the invention is achieved in this embodiment by mechanically restricting the maximum bending degree or converting the bending operation into a sufficiently large radius, which also prevents a plastic deformation of the plastic dimension or at least reduces it to a tolerable degree.

The arising forces that are greater than a possible maximum bending angle can be converted into longitudinal stress on the catheter shaft which is able to withstand said stress due to its material characteristics much better than bending forces.

Finally, it is fundamentally possible to form a spring on the proximal end of the catheter shaft, e.g. in the form of a flexible spiral spring which is connected to the fitting in the kink-prone region, so that the plastic deformation of the catheter shaft itself can also be prevented.

These and other objects, features, aspects and advantages of the present invention will become apparent to those skilled in the art from the following detailed description, which, taken in conjunction with the annexed drawings, discloses a preferred embodiment of the present invention.

BRIEF DESCRIPTION OF THE DRAWINGS

Referring now to the attached drawings which form a part of this original disclosure.

DETAILED DESCRIPTION OF THE PREFERRED EMBODIMENTS

Selected embodiments of the present invention will now be explained with reference to the drawings. It will be apparent to those skilled in the art from this disclosure that the following description of the embodiments of the present invention is provided for illustration only, and not for the purpose of limiting the invention as defined by the appended claims and their equivalents.

Figure 1:
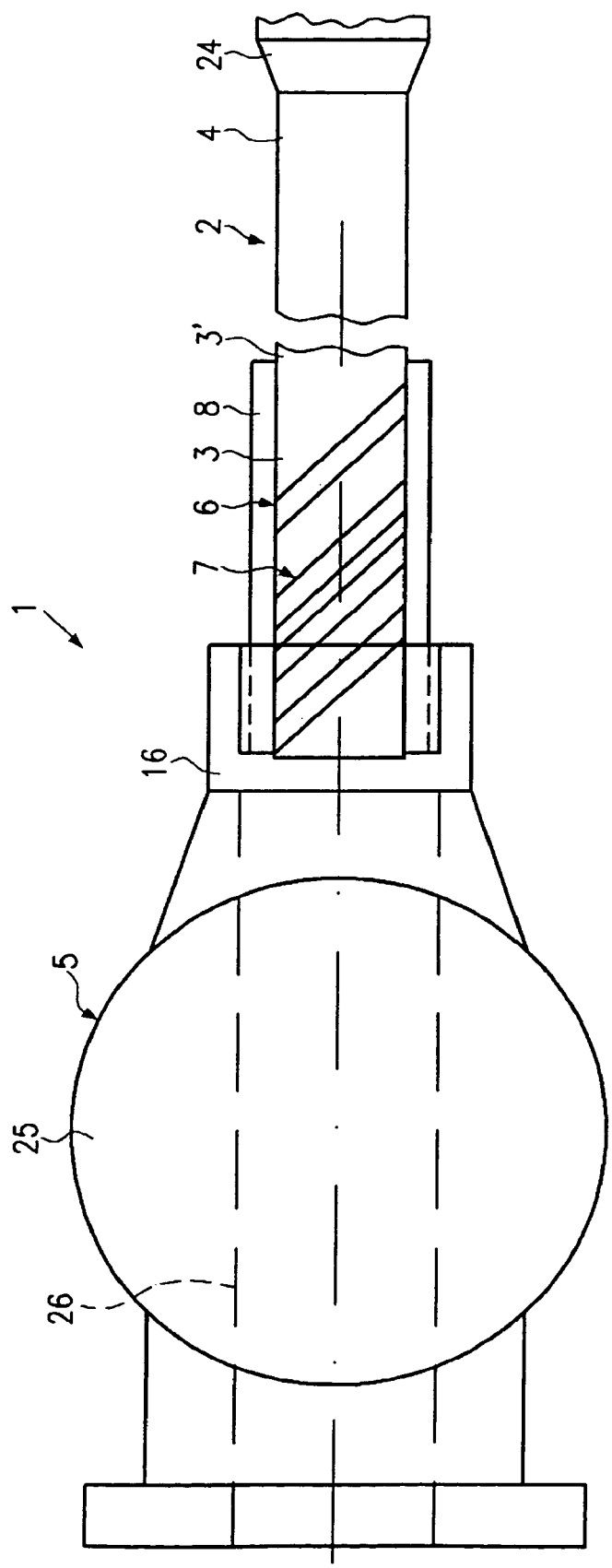
FIG. 1 is a schematically strongly simplified illustration of a catheter according to the present invention.

Referring initially to FIG. 1, a catheter 1 is illustrated in accordance with a first embodiment of the present invention. The catheter 1 of the present invention basically comprises a catheter shaft 2 provided with a proximal end 3 and a distal end 4, which are shown in FIG. 1 in a strongly shortened condition. A balloon 24, which is only illustrated schematically, is secured to the distal end 4. Furthermore, the catheter 1 comprises a fitting 5 which is normally designed as a luer fitting. The fitting 5 is secured to the proximal end 3 of the catheter shaft 2 and may comprise a housing 25 of a standard construction with a passageway 26 in flow communication with the catheter shaft 2. The fitting 5 is connected to a pressure device (inflation device) for expanding the balloon 24.

The proximal end 3 of the catheter shaft 2 of the catheter 1 according to the invention is provided with a bending section 6 having a flexibility greater than that of the section 3' of the catheter shaft 2 joining the proximal end 3. Said bending section 6 prevents unintended kinking in the way explained at the outset.

In the embodiment which is shown in FIG. 1 and particularly preferred, the bending section 6 is designed as a spiral 7 that is cut into the catheter shaft 2 and formed with a selectable number of spiral sections.

For preventing liquid from exiting, the spiral 7 is provided with a seal 8 which may be designed as a sleeve or tube that is secured, preferably by an adhesive, to the proximal section 3.

Figure 2:
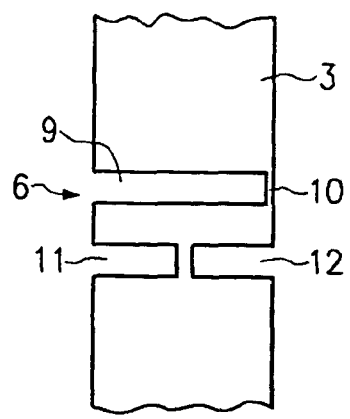
FIGS. 2 and 3 are illustrations corresponding to FIG. 1, which show possible designs of the bending section in the form of offset cuts.
Figure 3:
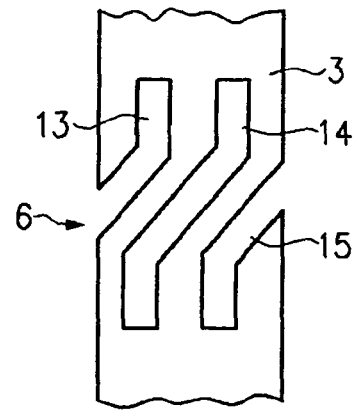

As illustrated in FIG. 1, the proximal end 3 is connected with its bending section 6 and the seal 8 arranged thereabove to a transition member 16 of the fitting 5, so that the region of the catheter shaft 2 that is prone to kinking is protected from unintended kinking FIGS. 2 and 3 show alternative embodiments of the bending section 6. In the embodiment shown in FIG. 2, the bending section 6 is formed at the proximal end 3 by a plurality of offset slits, which in the exemplary case are represented by two slits 9 and 11. The slits 9 and 11 extend up to webs 10 and 12, respectively, the arrangement of which yields the offset. The slits can be adapted in their dimensions (length, width, angular position) to different conditions of use.

In FIG. 3, the bending section 6 is also formed at the proximal end 3 by a plurality of offset slits 13, 14 and 15, which in this embodiment do not extend in circumferential direction as in FIG. 2, but extend essentially in the longitudinal direction of the proximal end 3. The slits 13 and 15 have two slit sections, of which one extends into the edge portion of the proximal end 3 while the slit 14 comprises three slit sections arranged at an angle relative to one another between slits 13 and 15.

Second Embodiment

Figure 4:
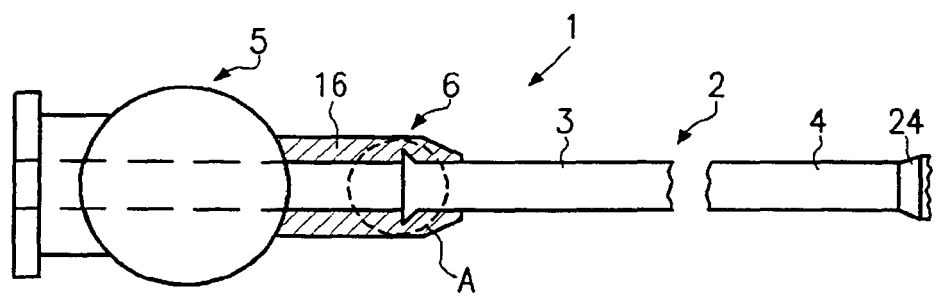
FIG. 4 is an illustration corresponding to FIG. 1, which shows a second embodiment of the catheter according to the present invention.
Figure 5:
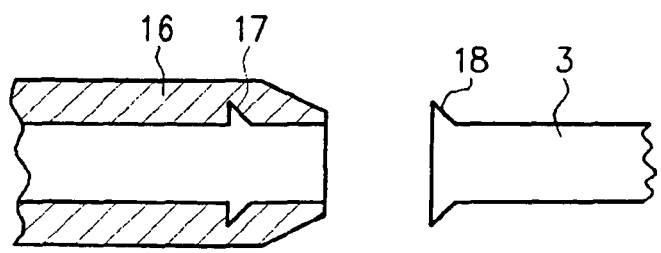
FIG. 5 is an enlarged illustration of detail A in FIG. 4.

Referring now to FIGS. 4 and 5, a catheter 1 in accordance with a second embodiment will now be explained. hi view of the similarity between the first and second embodiments, the parts of the second embodiment that are identical to the parts of the first embodiment will be given the same reference numerals as the parts of the first embodiment. Moreover, the descriptions of the parts of the second embodiment that are identical to the parts of the first embodiment may be omitted for the sake of brevity. Reference can here be made to the above explanations.

In the embodiment according to FIG. 4, the transition member 16 is formed as a flexible plastic section of the fitting 5 that is connected to the proximal end 3 of the catheter shaft 2. The detail according to FIG. 5 shows an undercut 17 which can be engaged by a holding member 18 of the proximal end 3 of the catheter shaft 2 for fixing the catheter shaft 2.

Third Embodiment

Figure 6:
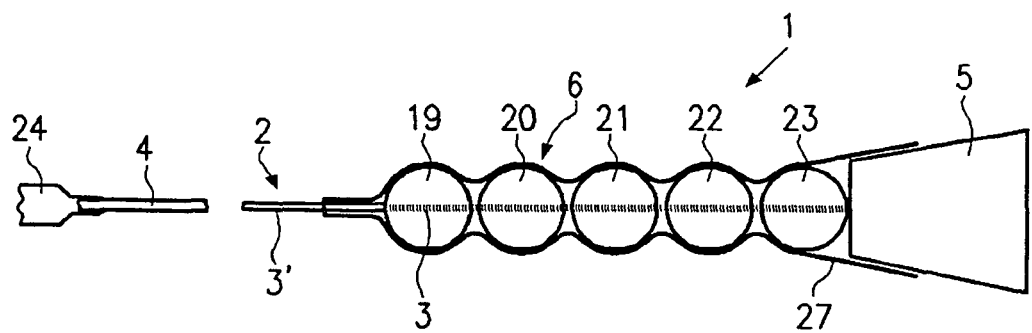
FIG. 6 is an illustration corresponding to FIG. 1, which shows a third, fundamentally possible embodiment of the catheter according to the invention.

Referring now to FIG. 6, a catheter 1 in accordance with a third embodiment will now be explained. In view of the similarity between the third and prior embodiments, the parts of the third embodiment that are identical to the parts of the prior embodiments will be given the same reference numerals as the parts of the prior embodiments. Moreover, the descriptions of the parts of the second embodiment that are identical to the parts of the first embodiment may be omitted for the sake of brevity. Reference can here be made to the above explanations.

In this embodiment, the bending section 6 comprises a plurality of balls 19 to 23 mounted on the proximal end 3. Said balls can be fixed to the catheter shaft 2 by way of different fastening possibilities as have been explained at the outset. In the embodiment shown in FIG. 6, a heat shrinkable tube 27 is provided for this purpose, said tube being connected at one end to the catheter shaft 2 and fixed at the other end to the fitting 5.

Figure 7:
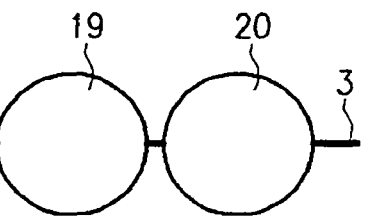
FIGS. 7-9 are illustrations showing parts of the catheter illustrated in FIG. 6, for explaining the function of the embodiment.
Figure 8:
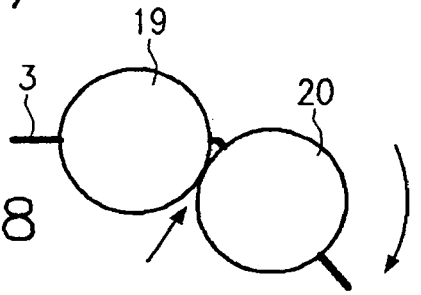
Figure 9:
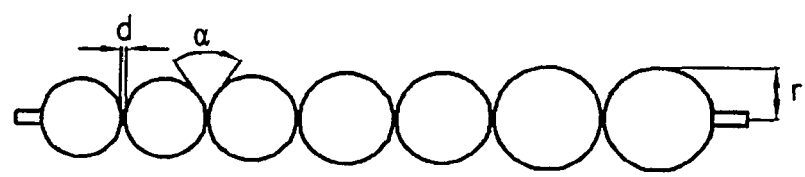

FIGS. 7 and 8 illustrate the function of the embodiment with reference to two balls 19 and 20. It becomes apparent that the balls can be dimensioned in their distance d and in their radius r (see FIG. 9) in such a way that a maximally acceptable bending angle a (see FIG. 9) is made possible. This angle a does not entail any plastic deformation and thus kinking or even breaking of the catheter shaft.

Catheters without a balloon shall also be regarded as catheters according to the invention.

The terms of degree such as "substantially", "about" and "approximately" as used herein mean a reasonable amount of deviation of the modified term such that the end result is not significantly changed. These terms should be construed as including a deviation of at least ±5% of the modified term if this deviation would not negate the meaning of the word it modifies.

This application claims priority to European Patent Application No. 02027767.9: The entire disclosure of European Patent Application No. 02027767.9 is hereby incorporated herein by reference.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. A medical device comprising:
   a catheter shaft having a proximal-most end, a distal end, and a section of the catheter shaft located distal to the proximal-most end of the catheter shaft;
   a balloon secured to the distal end;
   a luer fitting capable of being connected to a pressure device and arranged at the proximal-most end of the catheter shaft;
   the proximal-most end of the catheter shaft including a plurality of balls spaced to provide kink-free bending of the proximal-most end so as to avoid kinking the proximal-most end of the catheter shaft when removing the catheter shaft from packaging or when connecting the pressure device;
   the section of the catheter shaft located distal to the proximal-most end of the catheter shaft is less flexible than the proximal-most end of the catheter shaft; and
   a heat shrinkable tube disposed over the plurality of balls; wherein the heat shrinkable tube is connected at a first end to the catheter shaft and at a second end to the luer fitting.

2. The medical device of claim 1, wherein the plurality of balls are affixed to the catheter shaft by welding.

3. The medical device of claim 1, wherein the catheter shaft and the plurality of balls are one piece.

4. The medical device of claim 1, wherein a spacing of the plurality of balls is selected to define a maximum bending angle above which bending forces applied to the catheter shaft are converted to longitudinal stresses along the catheter shaft.

5. A medical device comprising:
   a hypotube having a proximal end and a distal end;
   a balloon secured to the distal end of the hypotube; and
   a fitting arranged at the proximal-most end of the hypotube, the proximal-most end of the hypotube including a bending section to provide kink-free bending of the proximal-most end, the bending section including a plurality of balls, wherein the plurality of balls are affixed to the hypotube using a heat shrinkable tube disposed over the plurality of balls and the heat shrinkable tube is connected at a first end to the hypotube and at a second end to the fitting.

6. The medical device of claim 5, wherein the plurality of balls are affixed to the hypotube by an adhesive bond.

7. The medical device of claim 5, wherein the plurality of balls are mechanically coupled to the hypotube.

8. The medical device of claim 5, wherein the plurality of balls are separated by a distance d and have a radius r to define a maximum acceptable bending angle $\alpha$.

9. The medical device of claim 8, wherein the angle $\alpha$ is selected to prevent kinking of the hypotube.

10. A medical device comprising:
    a catheter shaft having a proximal end and a distal end; and
    a luer fitting arranged at the proximal-most end of the catheter shaft, the proximal-most end of the catheter shaft including a plurality of balls spaced apart a distance d to provide kink-free bending of the proximal-most end of the catheter shaft; wherein a heat shrinkable tube is disposed over the plurality of balls, and the heat shrinkable tube is connected at a first end to the catheter shaft and at a second end to the luer fitting.

11. The medical device of claim 10, wherein a balloon is secured to the distal end of the catheter shaft.

12. The medical device of claim 10, wherein the catheter shaft includes a lumen and the luer fitting includes a passageway in fluid communication with the lumen.

13. The medical device of claim 10, wherein the plurality of balls are affixed to the catheter shaft by an adhesive bond or welding.

14. The medical device of claim 10, wherein the catheter shaft and the plurality of balls are one piece.

15. The medical device of claim 10, wherein the plurality of balls have a radius r, and the combination of the distance d and the radius r defines a maximum acceptable bending angle $\alpha$.

16. The medical device of claim 15, wherein the angle $\alpha$ is selected to prevent kinking of the catheter shaft.

* * * * *